United States Patent [19]

Leeson

[11] Patent Number: 4,758,427
[45] Date of Patent: Jul. 19, 1988

[54] ENHANCED ABSORPTION OF PSYCHOACTIVE 2-ARYL-PYRAZOLO QUINOLINES AS A SOLID MOLECULAR DISPERSION IN POLYVINYLPYRROLIDONE

[75] Inventor: Lewis J. Leeson, Roseland, N.J.

[73] Assignee: Ciba-Geigy Corporation, Ardsley, N.Y.

[21] Appl. No.: 6,297

[22] Filed: Jan. 20, 1987

Related U.S. Application Data

[63] Continuation-in-part of Ser. No. 763,489, Aug. 8, 1985, abandoned.

[51] Int. Cl.[4] ...................... A61K 17/00; A61K 31/47
[52] U.S. Cl. ...................................... 424/80
[58] Field of Search .................. 424/80; 514/293; 546/82, 162

[56] References Cited

U.S. PATENT DOCUMENTS

| | | | |
|---|---|---|---|
| 3,895,113 | 7/1975 | Omodei-Sale et al. | 514/293 |
| 4,038,476 | 7/1977 | Atasoy et al. | 424/80 |
| 4,259,331 | 3/1981 | Armstrong | 424/80 |
| 4,312,870 | 1/1982 | Yokoyama | 514/293 |
| 4,374,826 | 2/1983 | Armstrong | 424/80 |
| 4,524,146 | 6/1985 | Yokoyama | 514/293 |

FOREIGN PATENT DOCUMENTS 0012523  6/1980  European Pat. Off. ............ 424/80

Primary Examiner—Delbert R. Phillips
Assistant Examiner—Nathan M. Nutter
Attorney, Agent, or Firm—Irving M. Fishman

[57] ABSTRACT

The absorption of orally administered substantially aqueous insoluble psychoactive 2-aryl-pyrazolo [4,3-C] quinolin-3-ones of the formula

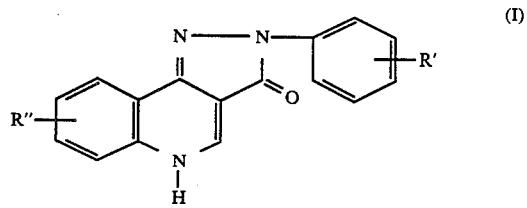

where R" is hydrogen, lower alkyl, lower alkoxy, hydroxy, halo or trifluoromethyl, and R' is hydrogen, lower alkyl, lower alkoxy, hydroxy, halo, trifluoromethyl, nitro, amino, mono- or di-lower alkylamino, mono- or di-lower alkylcarbamoylamino, mono- or di-lower alkylcarbamoyloxy or cyano, or a pharmaceutically acceptable salt thereof, is enhanced by administering the same in the form of a storage stable solid molecular dispersion of polyvinylpyrrolidone.

19 Claims, No Drawings

ENHANCED ABSORPTION OF PSYCHOACTIVE 2-ARYL-PYRAZOLO QUINOLINES AS A SOLID MOLECULAR DISPERSION IN POLYVINYLPYRROLIDONE

This application is a continuation-in-part of application Ser. No. 763,489, filed Aug. 8, 1983, now abandoned.

BACKGROUND OF THE INVENTION

The instant invention relates to solid molecular dispersions of one or more psychoactive substantially insoluble 2-aryl-pyrazolo [4,3-C]quinolin-3-ones in polyvinylpyrolidone (PVP) exhibiting enhanced absorption upon oral administration, and a method of treating anxiety or depression in mammals by orally administering to the mammal in need thereof an effective amount of such molecular dispersion.

The psychoactive 2-aryl-pyrazolo[4,3-C]quinolin-3-ones for use in preparing the molecular dispersions having enhanced absorption characteristics are described in U.S. Pat. No. 4,312,870, issued Jan. 26, 1982. In general, however, the psychoactive compounds and their pharmaceutically acceptable salts exhibit poor solubility characteristics in water, gastric fluid and intestinal fluid. Also such compounds tend to exhibit erratic absorption characteristics upon oral administration to mammals in conventional forms.

A number of studies are reported regarding the dissolution rates of various poorly soluble drugs in various polymer dispersions. For example, Simonelli et al., J. Pharm. Sci., 58(5), 538–549 (1969), discussed the increased rate of solution of sulfathiazole from tablets wherein the sulfathiaziole is previously coprecipitated with PV. As cautioned by the author, at Page 539 thereof, in order for the drug to be released from the polymer, the rate of solvent interation must be greater than the rate of intact complex dissolution, otherwise the drug will remain bound as a drug-polymer complex; and moreover, the rate of drug dissolution may be restricted by the amount of free drug in solution, for if the free drug concentration exceeds its solubility, precipitation of the unbound drug may occur on the surface of the dissolving complex, thereby adversely affecting further drug dissolution. Moreover, the stability of such two component systems is unpredictable since solid-solid phases may be unstable on storage, dur to the existence of a metastable system. This problem was recognized by Allen et al., J. Pharm. Sci., 58(10), 1190–1193 (1969). Accordingly, more complicated multi-component compositions have been proposed to increase the bioavailability of poorly soluble drugs. For example, U.S. Pat. No. 3,862,311, issued Jan. 21, 1975 discloses the combination of a drug, such as progesterone, a water soluble polymer and a nonionic surfactant, such as an ethylene oxide/propylene oxide polycondesate, to enhance in-vivo absorption of the drug.

It has now been found that psychoactive 2-arly-pyrazolo[4,3-C]quinolin-3-ones which are themselves substantially insoluble in water, gastric fluid and intestinal fluid can be formulated to substantially increase the bioavailability thereof upon oral administration by providing a solid molecular dispersion thereof in polyvinylpyrrolidone.

It is an object of the instant invention to provide such compositions.

It is a further object of the instant invention to provide a method of treating a mammal by the oral administration of such compositions.

It is yet a further object of the instant invention to provide methods for preparing such compositions.

These and other objects of the invention are apparent from the following detailed description of the invention.

DETAILED DESCRIPTION OF THE INVENTION

One embodiment of the invention relates to a solid oral dosage form comprising an effective anxiolytic or antidepresent amount of a stable solid molecular dispersion of a normally substantially aqueous insoluble psychoactive (a) compound of the formula

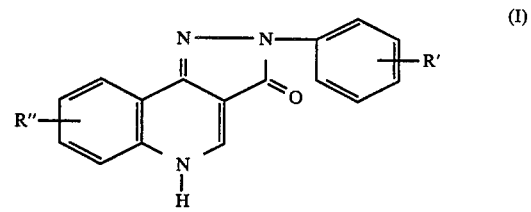

where R" is hydrogen lower alkyl, lower alkoxy, hydroxy, halo, or trifluoromethyl, and R' is hydrogen, lower alkyl, lower alkoxy, hydroxy, halo, trifluoromethyl, nitro, amino, mono- or di- lower alkylamino, mono- or di- lower alkylcarbamoylamino, mono- or dilower alkylcarbamoyloxy or cyano, or a pharmaceutically acceptable salt thereof, (b) in polyvinylpyrrolidone.

In respect to the definitions of R' and R" in the compounds of formula (I), the term, "lower" in each case preferably relates to those moieties wherein the alkyl group contains 1 to 4 carbon atoms. Similarly, by "halo" is preferably meant chloro, bromo, or fluoro.

Especially preferred antidepressant compounds of formula (I) are those wherein R" is hydrogen, alkyl, or alkoxy with up to 4 carbon atoms each, hydroxy, fluoro, chloro, bromo, or trifluoromethyl; and R' is hydrogen, o- or m-fluoro; or R" is p-fluoro when R" is chloro; or a pharmaceutically acceptable salt thereof.

Such preferred antidepressant compounds also exhibit apetite suppression characteristics rendering such psychoactive compounds highly useful in the treatment of obesity and the like, as see U.S. Pat. No. 4,459,298, issued July 10, 1084, the disclosure of which is hereby incorporated by reference.

Outstanding antidepression compounds of formula (I) are those wherein R" is hydrogen or 8-(methyl, methoxy, fluoro or chloro) and R' is hydrogen, or R' is 4-fluoro when R" is 8-chloro, or a pharmaceutically acceptable salt thereof. Most preferred is the compound wherein R" and R' are both hydrogen.

Especially preferred anxiolytic compounds of formula (I) are those wherein R" is hydrogen or 8-(methyl, methoxy, fluoro or chloro), and R' is 4-(methyl, methoxy, chloro, bromo, amino or cyano) or R' is 4-fluoro when R" is other than 8-chloro; or a pharmaceutically acceptable salt thereof. Most preferred anxiolytic compounds are those compounds wherein R" is hydrogen and R' is 4-chloro and wherein R" is 8-methoxy and R' is 4-fluoro.

Polyvinylpyrrolidone (PVP) is a synthetic polymer, well known in the art, which consists essentially of linear 1-vinyl-2-pyrrolidone groups, the degree of polymerization of which results in polymers of various molecular weights. The weight average molecular weight of suitable PVP polymers for use as component (b) in the present invention can vary widely, but are preferably at least about 4000. PV having a weight average molecular weight between about 4,000 and about 1,200,000 are highly advantageous, due to their general commercial availability. Highly preferred are PVP polymers having a weight average molecular weight between about 8,000 and 80,000, and most preferably between about 10,000 and 70,000.

The weight ratio of the psychoactive component (a) to the total molecular dispersion of component (a) plus the PV component, component (b), can very widely, but is characteristically limited by the amount of psychoactive component (a) capable of being molecularly dispersed within the PV matrix so as to result in a storage-stable composition capable of providing enhanced bioavailability of component (a).

Preferably, the weight percent of component (a) to the molecular dispersion of component (a) plus component (b) is within about 0.2 to about 20 weight percent, more preferably between about 0.5 and about 10 weight percent, and most preferably between about 0.7 and about 5 weight percent.

The solid composition, according to the present invention, of components (a) and (b) are in the form of a molecular dispersion of component (a) within the matrix of component (b), and may exist in the form of a solid solution, a supercooled liquid solution in solid state, or a sub-colloidal dispersion of component (a) within the matrix of component (b). In any event, the instant molecular dispersions are clearly divergent in dissolution properties from conventional micronized formulations and the like.

The instant molecular dispersions may be conveniently prepared by dissolving PVP in an aqueous, organic, or an aqueous/organic solvent medium, wherein the organic medium is a lower alkanol, such as methanol or ethanol, chloroform, dimethylsulfoxide, propylene glycol, 1-methyl-2-pyrrolidone, or the like, and adding thereto the psychoactive component (a) and removing the solvent therefrom. Conveniently, the aqueous, organic, or aqueous/organic PVP solution is maintained at an elevated temperature, e.g. between 30° C. and the boiling point of the solvent, preferably between 30° C. and 60° C., and component (a) is added thereto. The solution is then, after equilibration, allowed to cool, any residual precipitate of component (a) removed from the cooled solution, e.g., by filtration and the organic solvent removed, e.g., by evaporation, spray drying or the like, under ambient or reduced pressure. If desired, the solid molecular dispersion obtained can subsequently be granulated. Alternatively, the solution can be dried in the form of a film or layer in a formed substrate.

Alternatively, the component (a) may be simply dissolved in moltion PV and subsequently cooled to form the desired molecular dispersion. The molten solution may be cooled by spraying or placed into forms of convenient size and shape. Alternatively, the molten solution may be cooled in bulk and subsequently granulated.

A further alternative means of preparing the instant molecular dispersions is blending the active ingredient and polyvinylpyrrolidone (PVP) together, dissolving the blend in an appropriate solvent as set forth above, and subsequently removing the solvent.

Frequently, to effect a sufficient or a desirable degree of dissolution of the components in the solvent, a processing aid, for example mono, di and tri lower alkyl amines, such as monoethanolamine; and N,N-di(lower alkyl)-lower alkylcarbamoyls such as dimethylacetamide and N,N-di lower alkyl formamides such as dimethylformamide, etc. is used. In such a case the active agent and PVP components are preferably dissolved in a minimum amount of processing aid and the solution is diluted with a solvent mentioned above. When desirable, a solvent above can act as a processing aid for PV and another solvent listed above. The preparation proceeds by removing the solvent, during which step all or nearly all of the processing aid is removed. In the situation when the processing aid is a pharmaceutically acceptable entity, it need not be removed at all.

The applied dosage may range between 0.01 and 50 mg/kg/day preferably between about 0.02 and 3 mg/kg/day and advantageously between about 0.05 and 0.25 mg/kg/day.

The compositions in the form of molecular dispersions of the present invention may be incorporated into gelatin capsules or formulated into tablets, alone or in admixture with pharamceutically acceptable excipients, including conventional diluents, lubricants, binders, disinegrants, absorbents, colorants, flavors and sweeteners.

When formulated in admixture with such excipients, the excipients are combined with the instant solid molecular dispersions by conventional mixing, granulating or coating methods respectively, and generally contain between about 0.1 to about 99% by weight, preferably between about 1 to about 60% by weight of the excipient based on the weight of formulated composition.

The following examples, illustrating the invention, are not to be construed as limitations thereon. Temperatures are given in degrees centigrade, and all parts wherever given are parts by weights unless otherwise stated.

EXAMPLE 1

Forty (40.0) grams of polyvinylpyrrolidone having a weight average molecular weight of about 50,000 (USP Povidone K-30) is dissolved with stirring in absolute ethanol (USP Alcohol 3A) in an amount sufficient to result in a total solution volume of 100 ml, maintained at a temperature of about 40° C. To this solution there is slowly added 1.0 gram of 2-(p-chlorophenyl)-pyrazolo[4,3-C]quinolin-3(5H)-one with stirring and the resulting mixture is allowed to equilibrate with stirring at a temperature of about 40° C. for a period of 7 hours. The resulting solution is then allowed to cool to ambient temperature (about 18° C.) over a period of about 15 hours, and is filtered through a medium porosity scientered glass funnel with partial vacuum to remove any residual undissolved material. About 20 ml of additional absolute ethanol is added to the filtrate, and the filtrate is poured into a 9 inch by 13-inch glass pan and evaporated under ambient conditions to dryness. A clear yellow solid glass results and is placed in a mortar and pulverized. The pulverized material is then ground (through a Brinkman ZM-1 grinder) to yield a fine crystalline powder consisting of a molecular dispersion of 2-(p-chlorophenyl)pyrazolo[4,3-C]quinolin-3(5H)-one in the polyvinylpyrrolidone.

Assay results: 2.2 mg drug/100 mg total weight.
Approximate yield: 25 grams.

EXAMPLE 2

In a manner otherwise identical to Example 1, 1.0 grams of 2-(p-fluorophenyl)-8-methoxypyrazolo[4,3-C]quinolin-3(5H)-one is dissolved in 40.0 grams of polyvinylpyrrolidone/absolute ethanol having a total solution volume of 100 ml, which is subsequently equilibrated, cooled, filtered, dried, pulverized and ground to yield a fine crystalline powder consisting of a molecular dispersion of the drug in polyvinylpyrrolidone containing approximately 2.5 mg drug per 100 mg total weight.

EXAMPLE 3

In a manner otherwise identical to Example 1, 1.0 grams of 2-(phenyl)-pyrazolo[4,3-C]quinolin-3(5H)-one is dissolved in 40.0 grams of polyvinylpyrrolidone/absolute ethanol having a total solution volume of 100 ml, which is subsequently equilibrated, cooled, filtered, dried, pulverized and ground to yield a fine crystalline powder consisting of a molecular dispersion of the drug in polyvinylpyrrolidone containing approximately 2.5 mg drug per 100 mg total weight.

EXAMPLE 4

In order to determine the aqueous solubility characteristics of the instant molecular dispersions, 400 mg portions of the composition prepared according to Example 1 are filled into No. 0 hard gelatin capsules to obtain dosage forms containing 8.8 mg of drug per capsule. The dissolution rate of the encapsulated material is determined by placing a capsule into 1000 ml of distilled water which is maintained at 37° C. with stirring. Periodically, 2 ml aliquots of solution are removed from the stirred mixture, and analyzed to determine the amount of dissolved 2-(p-chlorophenyl)pyrazolo[4,3-C]quinolin-3(5H)-one present in the stirred mixture. The tabulated results are reported in Table I.

TABLE I

| Time (min) | Drug Dissolved (mg) | | |
|---|---|---|---|
| | Run 1 | Run 2 | Average |
| 10 | 1.95 | 0.82 | 1.39 |
| 20 | 2.15 | 1.35 | 1.75 |
| 30 | 4.18 | 2.23 | 3.21 |
| 45 | 5.56 | 3.96 | 4.76 |
| 60 | 5.81 | 4.78 | 5.30 |

EXAMPLE 5

In accordance with the method of Example 1, a solid molecular dispersion containing 0.4 mg of 2-(p-chlorophenyl)-pyrazolo[4,3-C]quinolin-3(5H)-one per 100 mg polyvinylpyrrolidone having a weight average molecular weight of about 50,000 is prepared. In order to determine the bioavailability of the dispersed drug, 30 grams of the solid dispersion, containing 12 mg. drug, is dissolved in sufficient distilled water to obtain 100 ml. solution, and intubated into the stomach of rats in a dosage amount, based on the active drug ingredient, of 1 mg per kg. rat body weight. For comparative purposes, a high surface area precipitate of 12 mg of 2-(p-chlorophenyl)-pyrazolo[4,3-C]quinolin-3(5H)-one is suspended in 100 ml of a solution containing 75 ml sucrose syrup USP (containing 85% sucrose in distilled water), 0.18 g methylparaben, 0.02 g propylparaben, and sufficient distilled water to obtain 100 ml suspension, and is likewise intubated into the stomach of test rats in a dosage amount, based on the active drug ingredient, of 1 mg per kg. rat body weight. In the following table, Table II, the results are summarized, rats 1, 2 and 3 receiving the drug/PVP solution and rats 4 and 5 receiving the drug/sucrose suspension.

TABLE II

| Rat No. | Plasma Concentration (ng/ml) Following Oral Administration of 1 mg/kg (Rat) | | | | | | | | |
|---|---|---|---|---|---|---|---|---|---|
| | 0 | 0.5 | 1 | 1.5 | 2 | 3 | 5 | 7 | AUC |
| 1 | 0 | 368 | 395 | 276 | 233 | 201 | 125 | 45 | 1291 |
| 2 | 0 | 408 | 303 | 275 | 225 | 131 | 111 | 62 | 1142 |
| 3 | 0 | 184 | 277 | 127 | 85 | 223 | 112 | 150 | 1066 |
| 4 | 0 | 89 | 34 | 21 | 41 | 49 | 65 | 89 | 395 |
| 5 | 0 | 54 | 34 | 438 | 26 | 37 | 39 | 101 | 517 |

*AUC represents the Area Under the Curve (0–7 hr) in ng × hr/ml.

EXAMPLE 6

Invention sample tablets (A) were prepared as follows: 50 g of 2-(4-chlorophenyl)-pyrazolo[4,3-c]quinolin-3-(5H)-one (active compound) and 450 g of polyvinylpyrrolidone (PVP) were blended for 5–10 minutes in a Hobart mixer and then dissolved in 100 g monoethanolamine. This was then diluted with 1500 ml 3A Alcohol. This solution was used to granulate 2000 g of Avicel PH 101 (microcrystalline cellulose-manufactured by FMC) and 85 g of Explotab (a modified starch supplied by Edward Mandel Company. The granules were screened and dried at 40° C. overnight.

The dried granules were then mixed, in a Hobart mixer for 10 minutes with an additional 170 g of Explotab. 30 g of magnesium stearate was then added with mixing for 5–10 minutes, after which the mixture was compressed into tablets (A).

Conventional tablets of the art (having PVP as a binder) were prepared as described above, except that no monoethanolamine was used, to result in tablets (C).

The finished tablets had the following compositions (in mg/tablet):

| Component | Invention [Tablet A] | Art [Tablet C] |
|---|---|---|
| active compound | 5 | 5 |
| PVP | 45 | 45 |
| monoethanolamine | 10 | — |
| 3A Alcohol | trace | trace |
| Avicel PH 101 | 200 | 200 |
| Explotab | 25.5 | 25.5 |
| Magnesium stearate | 3 | 3 |

A second invention tablet Sample (B) was prepared as follows:

50 g of the active compound above and 400 g PVP were mixed in a Hobart mixer for 5–10 minutes and dissolved in a minimum of dimethyl acetamide (DMA). The resulting viscous liquid was diluted with sufficient 3A Alcohol so the resulting alcoholic solution would be able to granulate 2500 g lactose. 2500 g of lactose was then granulated with the solution.

The granules were then screened and dried at 60° C. overnight and again screened and dried for 4 hours at 60° C. To the dried granules 295 g Explotab were added with mixing for 5–10 minutes. 35 g magnesium stearate were then added with additional mixing for 5–10 minutes. The mixture was then compressed into tablets (B).

Conventional tablets according to the art were formulated as follows:

50 g of the active agent were mixed with 2500 g lactose in a Hobart mixer for 5-10 minutes. The mixture was then granulated with an alcoholic solution of PVP (400 g PVP dissolved in sufficient 3A Alcohol to both dissolve the PVP and yield enough solution to granulate the above mixture). The granules were screened and dried at 40° C., and rescreened. 295 g Explotab were mixed with the dry granules for 5-10 minutes. Then, 35 g magnesium stearate were added and mixed for 5-10 minutes. The result was then compressed into tablets (D).

The finished tablets have the following compositions (in mg/tablet):

| Component | Invention (Tablet B) | Art (Tablet D) |
|---|---|---|
| Active Compound | 5 | 5 |
| PVP | 40 | 40 |
| DMA | Trace | — |
| 3A Alcohol | Trace | Trace |
| Lactose | 250 | 250 |
| Explotab | 29.5 | 29.5 |
| Magnesium Stearate | 3.5 | 3.5 |

1 tablet of each sample was placed in 1000 ml of distilled water at 37° C. and stirred using the USP paddles method at 50 RPM. The solution was sampled at various intervals and the sample analyzed by high performance liquid chromatography (HPLC). Values were obtained by comparison of the HPLC result with a standard curve obtained from dissolution media supplemented by known concentrations of active agent. The results are shown in the Table below:

TABLE 1

| | (% of active agent) | | | |
|---|---|---|---|---|
| Time | INVENTION A | ART C | INVENTION B | ART D |
| 10 min. | 27 | 13 | 39 | 29 |
| 20 min. | 48 | 18 | 63 | 41 |
| 30 min. | 75 | 19 | 78 | 44 |
| 60 min. | 98 | 20 | 91 | 50 |

The results show that invention Tablets A and B released almost all of the active agent with 1 hour; more than 4.5 times that of art Tablet C and nearly twice that of art Tablet D.

Furthermore, invention Tablet A released more active agent in 10 minutes than art Table C did after 1 hour. Similarly invention Tablet B released more active agent in 20 minutes than art Tablet D released in 1 hour.

What is claimed is:

1. A composition in a storage stable solid oral dosage form having enhanced absorption properties comprising an effective anxiolytic or antidepressant amount of a stable solid molecular dispersion consisting essentially of
   (a) a normally aqueous substantially insoluble psychoactive compound of the formula

[chemical structure]

where R" is hydrogen, lower alkyl, lower alkoxy, hydroxy, halo, or trifluormethyl and R' is hydrogen, lower alkyl, lower alkoxy, hydroxy, halo, trifluromethyl, nitro, amino, mono- or di- lower alkylamino, mono- or di- lower alkylcarbamoylamino, mono- or di- lower alkylcarbamoyloxy or cyano, or a pharmaceutically acceptable salt thereof
   (b) in polyvinylpyrrolidone.

2. A composition according to claim 1, wherein the polyvinylpyrrolidone has a weight average molecular weight of at least about 4,000.

3. A composition according to claim 2, wherein the ratio of component (a) to the molecular dispersion of component (a) plus component (b) is within about 0.2 to about 20 weight percent.

4. A composition according to claim 2, wherein said weight average molecular weight is between about 4,000 and about 1,200,000.

5. A composition according to claim 4, wherein said weight average molecular weight is between about 8,000 and about 80,000.

6. A composition according to claim 3, wherein said ratio is between about 0.5 and about 10 weight percent.

7. An antidepressant composition according to claim 1, wherein R" is hydrogen or 8-(methyl, methoxy, fluoro or chloro) and R' is hydrogen or R' is 4-fluoro when R" is 8-chloro.

8. A anxiolytic composition according to claim 1, wherein R" is hydrogen or 8-(methyl, methoxy, fluoro or chloro) and R' is 4-(methyl, methoxy, chloro, bromo, amino, or cyano) or R' is 4-fluoro when R" is other than 8-chloro.

9. A composition according to claim 7, wherein R" and R' are hydrogen.

10. A composition according to claim 8, wherein R" is hydrogen and R' is 4-chloro, or R" is 8-methoxy and R' is 4-fluoro.

11. A method of treating anxiety in a mammal which comprises the oral administration of an effective anxiolytic amount of a composition according to claim 1 to said mammal in need of the same.

12. A method of treating anxiety in a mammal which comprises the oral administration of an effective anxiolytic amount of a composition according to claim 8 to said mammal in need of the same.

13. A method of treating depression in a mammal which comprises the oral administration of an effective antidepressant amount of a composition according to claim 1 to said mammal in need of the same.

14. A method of treating depression in a mammal which comprises the oral administration of an effective antidepressant amount of a composition according to claim 7 to a mammal in need of the same.

15. The composition of claim 1 further comprising a trace to a minor amount of a processing aid which enhances the solubility of the compound of component (a) or polyvinylpyrrolidone or both in a polyvinylpyrrolidone aqueous, organic or aqueous/organic solvent medium.

16. The composition of claim 15 wherein said organic solvent medium is selected from a lower alkanol, chloroform, dimethylsulfoxide propylene glycol and 1-methyl- 2-pyrrolidone.

17. The composition of claim 15 wherein said processing aid is kimethylacetamide or monoethanolamine.

18. A process for the preparation of a composition of claim 1 comprising blending said compound and said polyvinylpyrrolidone to form a blend, dissolving said blend in a processing aid to effect a first solution, diluting said first solution with a solvent selected from lower alkanol, chloroform, dimethylsulfoxide propylene glycol and 1-methyl-2-pyrrolidone to form a second solution, and removing said solvent to form the composition of claim 1.

19. The process of claim 18 further comprising granulating a pharamceutically acceptable excipient with said second solution before removing said solvent therefrom.

* * * * *